(12) United States Patent
Schaafsma

(10) Patent No.: US 9,120,709 B2
(45) Date of Patent: Sep. 1, 2015

(54) METHOD OF MAKING CONTROLLED RELEASE FERTILIZER PARTICLES

(71) Applicant: Stamicarbon B.V., Sittard (NL)

(72) Inventor: Stefan Hendrikus Schaafsma, Sittard (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 14/354,125

(22) PCT Filed: Oct. 24, 2012

(86) PCT No.: PCT/NL2012/050741
§ 371 (c)(1),
(2) Date: Apr. 24, 2014

(87) PCT Pub. No.: WO2013/062410
PCT Pub. Date: May 2, 2013

(65) Prior Publication Data
US 2014/0260469 A1    Sep. 18, 2014

(30) Foreign Application Priority Data

Oct. 24, 2011    (EP) .................... 11186395

(51) Int. Cl.
| | |
|---|---|
| C05G 3/10 | (2006.01) |
| C05C 9/00 | (2006.01) |
| B29B 9/10 | (2006.01) |
| C05G 3/00 | (2006.01) |
| A61K 9/16 | (2006.01) |
| B01J 2/02 | (2006.01) |
| B01J 2/26 | (2006.01) |

(52) U.S. Cl.
CPC ............ *C05G 3/0088* (2013.01); *A61K 9/1694* (2013.01); *B01J 2/02* (2013.01); *B01J 2/26* (2013.01); *C05G 3/0029* (2013.01)

(58) Field of Classification Search
None
See application file for complete search history.

(56) References Cited

U.S. PATENT DOCUMENTS

| 7,700,012 B2 | 4/2010 | Van Der Werf et al. |
| 7,931,729 B2 | 4/2011 | Santosh |
| 2007/0131381 A1 | 6/2007 | Schermutzki et al. |

FOREIGN PATENT DOCUMENTS

| EP | 2 353 708 | 8/2011 |
| EP | 2 353 709 | 8/2011 |
| WO | WO-2009/023235 | 2/2009 |

OTHER PUBLICATIONS

International Search Report for PCT/NL2012/050741, mailed 17 Dec. 2012, 3 pages.

*Primary Examiner* — Wayne Langel
(74) *Attorney, Agent, or Firm* — Morrison & Foerster LLP

(57) ABSTRACT

The invention pertains to a method of making urea-containing particles wherein with a lower degree of cooling, high mechanical strengths are obtained. The method comprises the steps of (a) providing a first polymer 10 layer; (b) feeding urea droplets onto said first polymer layer, (c) cooling the droplets provided on the first polymer layer to a temperature between 55° C. and 120° C.; (d) applying a second polymer layer onto the first polymer layer comprising the droplets so as to form encapsulated urea droplets; and (e) separating the encapsulated urea droplets.

13 Claims, No Drawings

METHOD OF MAKING CONTROLLED
RELEASE FERTILIZER PARTICLES

CROSS-REFERENCE TO RELATED
APPLICATIONS

This application is the national phase of PCT application PCT/NL2012/050741 having an international filing date of 24 Oct. 2012, which claims benefit of European patent application No. 11186395.7 filed 24 Oct. 2011. The contents of the above patent applications are incorporated by reference herein in their entirety.

FIELD OF THE INVENTION

The invention relates to a method of making urea-containing particles.

BACKGROUND OF THE INVENTION

A method of making urea-containing particles is known from U.S. Pat. No. 7,700,012. Therein the urea comprising particles are produced in a pelletizer comprising a feeding device, a belt and a device to remove the formed pellets from the belt, by feeding a urea comprising liquid to the feeding device from which droplets of the urea comprising liquid are dosed to the belt. Thereon the urea comprising droplets solidify and cool to a temperature which is required to be 55° C. or lower, after which the formed urea comprising particles are removed from the belt. The cooling to below 55° C. is taught to be essential in order to obtain the necessary mechanical strength to handle the particles and to prevent abrasion and dust formation. Although this is significantly below the melting temperature of urea (around 132° C.), above 55° C. the granulate does not have enough strength, is more sticky and generates dust. The stickiness leads to fouling of the equipment and consequently lower on stream times. This temperature requirement leads in practice to very large and costly equipment due to the required residence time on the belt and at the same time restricts the size of the droplets to be formed. Alternatively it leads to the need for a very low temperature cooling medium, e.g. liquid nitrogen, which adds to operating cost.

Another reference relating to particles comprising urea is U.S. Pat. No. 7,931,729. The latter reference does not address mechanical strength of urea-comprising particles. Rather, it addresses an issue related to the use of urea as a fertilizer, by providing controlled release fertilizer particles in the form of polymer-encapsulated fertilizer, such as urea. To this end, the fertilizer is deposited onto a first polymer film and then covered by a second polymer film to encapsulate the fertilizer between the first polymer film and the second polymer film. The method can be carried out on a rotoformer, which is a device with a moving belt, a feeding device, feeding droplets onto the belt, wherein the belt is cooled. The cooling of the fertilizer droplets is disclosed to be to room temperature, i.e. as is convention in accordance with U.S. Pat. No. 7,700,012. The cooling of the fertilizer makes it easier to cut apart the encapsulated fertilizer droplets.

It would be desired to provide urea-containing particles that have a mechanical strength, and absence of dust formation, at least at about the level of the particles formed by cooling in U.S. Pat. No. 7,700,012. Yet, it would be desired to be able to avoid the aforementioned drawbacks of the cooling as disclosed.

SUMMARY OF THE INVENTION

In order to better address the foregoing desires the invention, in one aspect, provides a method of making urea-containing particles comprising the steps of (a) providing a first polymer layer; (b) feeding urea droplets onto said first polymer layer, (c) cooling the droplets provided on the first polymer layer to a temperature between 55° C. and 120° C.; (d) applying a second polymer layer onto the first polymer layer comprising the droplets so as to form encapsulated urea droplets; and (e) separating the encapsulated urea droplets.

In another aspect, the invention provides polymer-encapsulated urea particles obtainable by a process as described in the foregoing paragraph,

DETAILED DESCRIPTION OF THE INVENTION

The invention is based on the judicious recognition that a technique, of encapsulating urea particles in a polymer, is capable of solving the problems associated with the strong cooling otherwise required to make urea particles of sufficient mechanical strength. To this end, the inventors have identified that cooling between 55° C. and 120° C. when using the polymer-encapsulation technique, result in strong, non-dusting particles, and the temperatures involved serve to solve the disadvantages of strong cooling. The foregoing is all the more surprising, since the technique had been developed for an entirely different purpose. Preferably, the temperature is in the range of from 60° C. to 115° C., more preferably 65° C. to 100° C., and most preferably 70° C. to 90° C.

Urea can be provided in a known manner. A frequently used process for the preparation of urea according to a stripping process is the carbon dioxide stripping process as for example described in Ullmann's Encyclopedia of Industrial Chemistry, Vol. A27, 1996, pp 333-350.

The urea droplets can be provided in the form of a urea-containing solution, a urea-containing slurry, or a urea-containing melt. Preferably, the urea droplets are a urea melt, i.e. substantially pure urea (more than 99% urea, preferably more than 99.7% urea), at a temperature of above the melting point of urea, which under atmospheric conditions is 132° C. The urea preferably is a urea melt as obtained directly (i.e. preferably without separate isolation and/or cooling steps) after a urea production process. Optionally, the urea droplets comprise additives and/or other fertilizers in the same manner as disclosed in U.S. Pat. No. 7,700,012.

The polymer can be any film forming polymer. Suitable polymers are for example polyolefins such as polyethylene (PE), polypropylene (PP) and polystyrene (PS). Other suitable polymers include nylons (PA) for example PA6 and PA66 or polyesters such as polyethyleneterephthalate (PET), polybuthyleneterephthalate (PBT) and others. A preferred polymer is polyethylene. The first and second polymers can be the same or different. Preferably, they are the same. The polymer films may have a thickness of 10 to 100 µm, preferably 15 to 80 µm, more preferably 20 to 50 µm, for example about 30 µm.

The polymer films may be provided in different ways, for example on a roll or may be prepared in situ for example by extrusion or spraying. The first and the second polymer layer may provided in different ways, for example the first polymer layer may be provided from a roll while the second layer may be provided by direct extrusion or by spraying.

It is preferred that the first polymer layer is in planar motion when the urea droplets are applied. By planar motion reference is made to motion into a direction parallel to the plane of the polymer film. Preferably, the motion is longitudinal planar motion, such as on a moving belt. In these embodiments it is possible that the polymer is applied onto a moving belt, or that a polymer layer is made to move on a belt, whilst the belt stands still. In the event that neither the polymer layer nor the belt is in motion, it is preferred for a droplets-feeding device to be in motion so as to spread the droplets well over the surface of the polymer layer. The material of construction of the belt is not critical. Suitable materials may be for example metal or textile.

The process of the invention is preferably carried out on any device having a suitable feeder for urea droplets, a moving belt, and a suitable remover for urea particles. A preferred apparatus is a Rotoformer, ex Sandvik, as discussed in both U.S. Pat. Nos. 7,700,012 and 7,931,729. Also suitable is the pastillation equipment sold by Kaiser SBS.

After the application of the urea droplets, the same are brought down to a temperature of from 55° C. to 120° C. Preferably, the temperature is in the range of from 60° C. to 115° C., more preferably 65° C. to 100° C., and most preferably 70° C. to 90° C.

This cooling, as will be understood by the skilled person, is significantly more moderate than the cooling required in the art. The cooling can be done by providing a cooling atmosphere around the polymer, by cooling the polymer itself, but preferably it is done by providing the polymer onto a belt, and cooling the belt. The latter can be done by means of cooling water, or another cooling fluid. In another embodiment the urea droplets may be deposited on a cold plate covered with the first polymer film, wherein the film is being moved over the plate (i.e. a plate with a moving film, rather than a belt).

Another advantage of the process of the invention is that there is no direct contact between the urea and the moving belt preventing fouling. This is of particular importance since the problem of fouling is worse at higher temperatures, such as in the range of from 55° C. to 120° C., due to stickiness of the urea.

The feeder can be any device capable of distributing droplets of a liquid. Preferably a screen is used with holes through which the urea liquid is pressed, or a rotating cylindrical drum with holes.

A second polymer film is applied over the droplets in a similar way as described in U.S. Pat. No. 7,931,729, i.e. by applying a film or by spraying a polymer.

An advantage of the process of the invention is that it is possible to produce high quality controlled release fertilizer pellets that have mechanical integrity, good crushing strength and allow handling without generating dust. Another advantage is that it is possible to use produce larger size droplets without the need to use extremely low cooling medium temperatures.

In connection herewith the invention, in another aspect, provides polymer-encapsulated urea particles obtainable by a process as described in the foregoing paragraph.

The invention claimed is:

1. A method of making urea-containing particles comprising the steps of:
   (a) providing a first polymer layer;
   (b) feeding urea droplets onto said first polymer layer;
   (c) cooling the droplets provided on the first polymer layer to a temperature in the range of from 60° C. to 115° C. and maintaining the temperature while performing step (d) in the range of from 60° C. to 115° C.;
   (d) applying a second polymer layer onto the first polymer layer comprising the droplets so as to form encapsulated urea droplets; and
   (e) separating the encapsulated urea droplets.

2. A method according to claim 1, wherein the urea droplets are in the form of a urea melt.

3. A method according to claim 1, wherein the cooling and maintaining is in the range of 70° C. to 90° C.

4. A method according to claim 1, wherein the first polymer layer is in planar motion when feeding the urea droplets onto said first polymer layer.

5. A method according to claim 4, wherein said planar motion is in a longitudinal direction.

6. A method according to claim 4, wherein the motion is provided by applying the first polymer layer onto a moving belt.

7. A method according to claim 6, wherein the cooling is provided by cooling the belt.

8. A method according to claim 1, conducted on a Rotoformer.

9. A method according to claim 4, wherein the motion is provided by allowing a film of the first polymer to move over a plate.

10. A method according to claim 9, wherein the cooling is provided by cooling the plate.

11. A method according to claim 1, wherein the first polymer and the second polymer independently are selected from the group consisting of polyethylene, polypropylene, polyester and polyamide.

12. A method according to claim 1, wherein the first and second polymers are the same.

13. A method according to claim 1 wherein the cooling and maintaining is in the range of from 65° C. to 100° C.

* * * * *